(12) United States Patent
Kawana et al.

(10) Patent No.: US 10,335,110 B2
(45) Date of Patent: Jul. 2, 2019

(54) RADIOGRAPHIC IMAGE CAPTURING SYSTEM AND RADIOGRAPHIC IMAGE CAPTURING APPARATUS

(71) Applicant: Konica Minolta, Inc., Chiyoda-ku, Tokyo (JP)

(72) Inventors: Yuki Kawana, Hino (JP); Hideaki Tajima, Hachioji (JP); Shugo Ishizaka, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 246 days.

(21) Appl. No.: 15/492,487

(22) Filed: Apr. 20, 2017

(65) Prior Publication Data

US 2017/0303883 A1    Oct. 26, 2017

(30) Foreign Application Priority Data

Apr. 22, 2016   (JP) .................................. 2016-085653

(51) Int. Cl.
    *A61B 6/00*     (2006.01)
    *H04N 5/32*     (2006.01)

(52) U.S. Cl.
    CPC ................. *A61B 6/54* (2013.01); *A61B 6/42* (2013.01); *A61B 6/4283* (2013.01); *A61B 6/4405* (2013.01); *A61B 6/4452* (2013.01); *A61B 6/461* (2013.01); *A61B 6/5205* (2013.01); *A61B 6/585* (2013.01); *H04N 5/32* (2013.01)

(58) Field of Classification Search
    CPC ....... A61B 6/42; A61B 6/4283; A61B 6/4405; A61B 6/4452; A61B 6/461; A61B 6/5205; A61B 6/54; A61B 6/585; H04N 5/32
    See application file for complete search history.

(56) References Cited

U.S. PATENT DOCUMENTS

| 2012/0132820 A1* | 5/2012 | Iwakiri | ................. G01T 1/2018 250/370.08 |
| 2012/0132824 A1* | 5/2012 | Nishino | .................... H04N 5/32 250/394 |
| 2012/0217410 A1* | 8/2012 | Amitani | .................... H04N 5/32 250/370.09 |

(Continued)

FOREIGN PATENT DOCUMENTS

| JP | 2008022520 A | 1/2008 |
| JP | 2010088015 A | 4/2010 |

*Primary Examiner* — Mark R Gaworecki
(74) *Attorney, Agent, or Firm* — Cantor Colburn LLP

(57) ABSTRACT

A radiographic image capturing system includes the following. A radiographic image capturing apparatus includes a two-dimensional array of radiation detecting elements and a control circuit which controls reading of image data from each of the radiation detecting elements based on a predetermined capturing sequence. An image processor has first gain data to correct gains of the radiation detecting elements, and generates a radiographic image based on the corrected image data. The control circuit of the radiographic image capturing apparatus is capable of varying at least one of a reverse bias voltage and a signal line voltage to be applied to the corresponding signal line. The control circuit reads a signal value from each of the radiation detecting elements, creates second gain data based on the read signal value, and corrects the radiographic image with the first gain data and the second gain data.

5 Claims, 13 Drawing Sheets

(56) References Cited

U.S. PATENT DOCUMENTS

| | | | |
|---|---|---|---|
| 2013/0038738 A1* | 2/2013 | Ando | A61B 6/4266 348/162 |
| 2013/0071000 A1* | 3/2013 | Takagi | A61B 6/4233 382/132 |
| 2014/0119509 A1* | 5/2014 | Kaneko | A61B 6/4233 378/62 |
| 2014/0124678 A1* | 5/2014 | Yoneyama | A61B 6/4283 250/393 |
| 2014/0239189 A1* | 8/2014 | Sakino | H04N 5/32 250/394 |
| 2017/0290558 A1* | 10/2017 | Kikuchi | H04N 5/32 |

* cited by examiner

| RADIATION DETECTING ELEMENT 7 | REFERENCE GAIN DATA ast | OFFSET DATA O |
|---|---|---|
| (1,1) | $ast_{11}$ | $O_{11}$ |
| (1,2) | $ast_{12}$ | $O_{12}$ |
| (1,3) | $ast_{13}$ | $O_{13}$ |
| ⋮ | ⋮ | ⋮ |
| (2,1) | $ast_{21}$ | $O_{21}$ |
| (2,2) | $ast_{22}$ | $O_{22}$ |
| (2,3) | $ast_{23}$ | $O_{23}$ |
| ⋮ | ⋮ | ⋮ |

| RADIATION DETECTING ELEMENT 7 | READOUT EFFICIENCY Ero(m) | | | |
|---|---|---|---|---|
| | 1 | 2 | 3 | ... |
| (1,1) | $Ero(1)_{11}$ | $Ero(2)_{11}$ | $Ero(3)_{11}$ | ... |
| (1,2) | $Ero(1)_{12}$ | $Ero(2)_{12}$ | $Ero(3)_{12}$ | ... |
| (1,3) | $Ero(1)_{13}$ | $Ero(2)_{13}$ | $Ero(3)_{13}$ | ... |
| ⋮ | ⋮ | ⋮ | ⋮ | ⋮ |
| (2,1) | $Ero(1)_{21}$ | $Ero(2)_{21}$ | $Ero(3)_{21}$ | ... |
| (2,2) | $Ero(1)_{22}$ | $Ero(2)_{22}$ | $Ero(3)_{22}$ | ... |
| (2,3) | $Ero(1)_{23}$ | $Ero(2)_{23}$ | $Ero(3)_{23}$ | ... |
| ⋮ | ⋮ | ⋮ | ⋮ | ⋮ |

D*

D*

RADIOGRAPHIC IMAGE CAPTURING SYSTEM AND RADIOGRAPHIC IMAGE CAPTURING APPARATUS

CROSS REFERENCE TO RELATED APPLICATIONS

The present invention claims priority under 35 U.S.C. § 119 to Japanese Application No. 2016-085653, filed Apr. 22, 2016, the entire content of which is incorporated herein by reference.

BACKGROUND OF THE INVENTION

Field of the Invention

The present invention relates to radiographic image capturing systems and radiographic image capturing apparatuses.

Description of Related Art

A variety of radiographic image capturing apparatuses have been developed that generate electric charges at radiation detecting elements in proportion to the dose of emitted radiation and read the generated electric charges in the form of image data. These radiographic image capturing apparatuses are known as flat panel detectors (FPDs). The traditional radiographic image capturing apparatuses are of a dedicated (stationary) type integrated with their holders. Recently, radiographic image capturing apparatuses of a portable type (also referred to as "cassette type") have been developed, each including radiation detecting elements accommodated in a housing (For example, refer to Japanese Unexamined Patent Application Publication No. 2010-88015).

Multiple application of radiation on a traditional silver halide photographic display or film or a computed radiography (CR) cassette with a built-in photostimulable phosphor sheet cause double or multiple exposure in radiographic image capturing. In contrast, the radiographic image capturing apparatus described above can store captured image data in a storage and transfer the image data to an external device through a wireless or wired network. The radiographic image capturing apparatus thus can be used for videographic capturing without a risk of the double exposure.

In the following description, the term "videographic capturing" refers to capturing multiple radiographic images by applying pulsed radiation several times or sequentially applying radiation to the radiographic image capturing apparatus. Besides normal videographic capturing, the videographic capturing includes dynamic image capturing, tomosynthesis, and dual energy subtraction. Hereinafter, the term "still-image capturing" refers to capturing a single radiographic image by single application of radiation to the radiographic image capturing apparatus, and the term "still image" refers to a radiographic image captured by the still-image capturing.

The radiation detecting elements in the radiographic image capturing apparatus have different characteristics; for example, after the application of radiation to each radiation detecting element at the same dose, image data items D read from the radiation detecting elements generally have different values. To cope with this problem, the radiographic image capturing apparatus is evenly irradiated with radiation in absence of a subject before the factory shipment, for example, so that image data items D are read from the radiation detecting elements.

Before or after reading of the image data items D, offset data O based on dark electric charges (also referred to as "dark current") are read from the radiation detecting elements without application of radiation to the radiographic image capturing apparatus. The read image data items D are corrected in accordance with the following Expression (1) to generate corrected image data items D*. Gain data a for the correction of the gains of the radiation detecting elements are determined such that the corrected read image data items D* have an identical value.

$$D^* = a \times (D - O) \tag{1}$$

If the gain data a is determined through a sequence (or procedure) for still-image capturing with the radiographic image capturing apparatus, correction of the image data items D read from the radiation detecting elements of the radiographic image capturing apparatus d in absence of a subject through the same capturing sequence with the gain data a provides corrected image data items D* having a substantially identical value, despite slight variations due to noise, as shown in FIG. 17A.

In contrast, correction of the image data items D for one radiographic image read from the radiation detecting elements through a videographic capturing sequence (for example, dynamic-image capturing sequence) involving repeated alternation between application of radiation to the radiographic image capturing apparatus and reading of the image data items D with the gain data a provides the corrected image data items D* which do not necessarily have a substantially identical value, causing errors or uneven image density of several percent, as shown in FIG. 17B. FIGS. 17A and 17B illustrate the density of the corrected image data items D* with emphasis.

This demonstrates that the gain data a for the image data items D captured through the still-image capturing sequence with the radiographic image capturing apparatus should not be applied to the image data items D captured through the videographic capturing sequence with the radiographic image capturing apparatus. Japanese Unexamined Patent Application Publication No. 2008-22520, for example, discloses a radiographic image capturing apparatus performing multiple capturing sequences (a still-image capturing mode and videographic capturing modes 1 to 3 in this patent literature). The radiographic image capturing apparatus has correction information or gain data a for the capturing sequences. The radiographic image capturing apparatus selects appropriate correction information from the multiple pieces of correction information based on the capturing sequence actually performed, and then applies the selected correction information to image data items D to be corrected.

Unfortunately, the technique disclosed in Japanese Unexamined Patent Application Publication No. 2008-22520 has the following disadvantages: The radiographic image capturing apparatus which is operated in several modes, such as still-image capturing, normal videographic capturing, dynamic-image capturing, tomosynthesis and dual energy subtraction, needs to acquire the gain data a for each capturing sequence before the factory shipment. This leads to disadvantages, such as a long-time operation before the shipment, the need for storing the gain data a corresponding to the capturing sequences, and a difficulty in adding a different capturing sequence.

In the case of variations in temperature in the radiographic image capturing apparatus, the images captured through the still-image capturing have a uniform image density, whereas the images captured through the videographic capturing have an uneven image density even after the correction with the gain data a acquired through the videographic capturing sequence. To address this problem, the radiographic image capturing apparatus should acquire much more gain data a for multiple temperatures before the factory shipment and selects or interpolates the gain data a appropriate for the temperature of a panel.

To solve the above problem, the gain data a corresponding to the temperature of a panel of the radiographic image capturing apparatus may be acquired, for example, before capturing of a diagnostic image. However, the acquisition of the gain data a requires execution of image capturing involving actual application of radiation to the entire surface of the panel of the radiographic image capturing apparatus and determination of the gain data a such that the corrected image data items D* from the radiation detecting elements have an identical value, by a radiological technician. This operation should be conducted each time the panel temperature varies, and therefore is very burdensome.

BRIEF SUMMARY OF THE INVENTION

An object of the present invention, which has been made in view of the problems described above, is to provide a radiographic image capturing system and a radiographic image capturing apparatus capable of automatically and properly calculating gain data for correction of image data items read from the radiation detecting elements of the radiographic image capturing apparatus without the need for the operation by a radiological technician.

According to an aspect of the present invention, there is provided a radiographic image capturing system including: a radiographic image capturing apparatus including: a two-dimensional array of radiation detecting elements which each have a first electrode and a second electrode; and a control circuit which controls reading of image data from each of the radiation detecting elements based on a predetermined capturing sequence; and an image processor which has first gain data to correct gains of the radiation detecting elements in the radiographic image capturing apparatus, which corrects the image data based on the first gain data, and which generates a radiographic image based on the corrected image data, wherein a reverse bias voltage is applied to the first electrode of each of the radiation detecting elements of the radiographic image capturing apparatus, a corresponding signal line is connected to the second electrode of each of the radiation detecting elements via a switching element, the control circuit of the radiographic image capturing apparatus is capable of varying at least one of the reverse bias voltage and a signal line voltage to be applied to the corresponding signal line, and after resetting of the radiation detecting elements, the control circuit reads a signal value from each of the radiation detecting elements by varying at least one of the reverse bias voltage and the signal line voltage, creates second gain data based on the read signal value, and corrects the radiographic image with the first gain data and the second gain data.

According to another aspect of the present invention, there is provided a radiographic image capturing apparatus including: a two-dimensional array of radiation detecting elements which each have a first electrode and a second electrode; and a control circuit which controls reading of image data from each of the radiation detecting elements based on a predetermined capturing sequence, wherein a reverse bias voltage is applied to the first electrode of each of the radiation detecting elements, a corresponding signal line is connected to the second electrode of each of the radiation detecting elements via a switching element, the control circuit has first gain data to correct gains of the radiation detecting elements, corrects the image data based on the first gain data, and generates a radiographic image based on the corrected image data, the control circuit is capable of varying at least one of the reverse bias voltage and a signal line voltage to be applied to the corresponding signal line, and after the resetting of the radiation detecting elements, the control circuit reads a signal value from each of the radiation detecting elements by varying at least one of the reverse bias voltage and the signal line voltage, creates second gain data based on the read signal value, and corrects the radiographic image with the first gain data and the second gain data.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

Embodiments of a radiographic image capturing system and a radiographic image capturing apparatus according to the present invention will now be described with reference to the accompanying drawings.

In the following description, the radiographic image capturing apparatus is of an indirect type, which includes a scintillator. The indirect radiographic image capturing apparatus converts incident radiation into electromagnetic waves with a different wavelength, such as visible light, to generate electric signals. Alternatively, the radiographic image capturing apparatus may be of a direct type, which detects radiation directly with detecting elements without using a scintillator.

In the following description, the radiographic image capturing apparatus is of a portable type. Alternatively, the radiographic image capturing apparatus may be of a dedicated type, which is integrated with a holder.

[Radiographic Image Capturing Apparatus]

Figure 1:
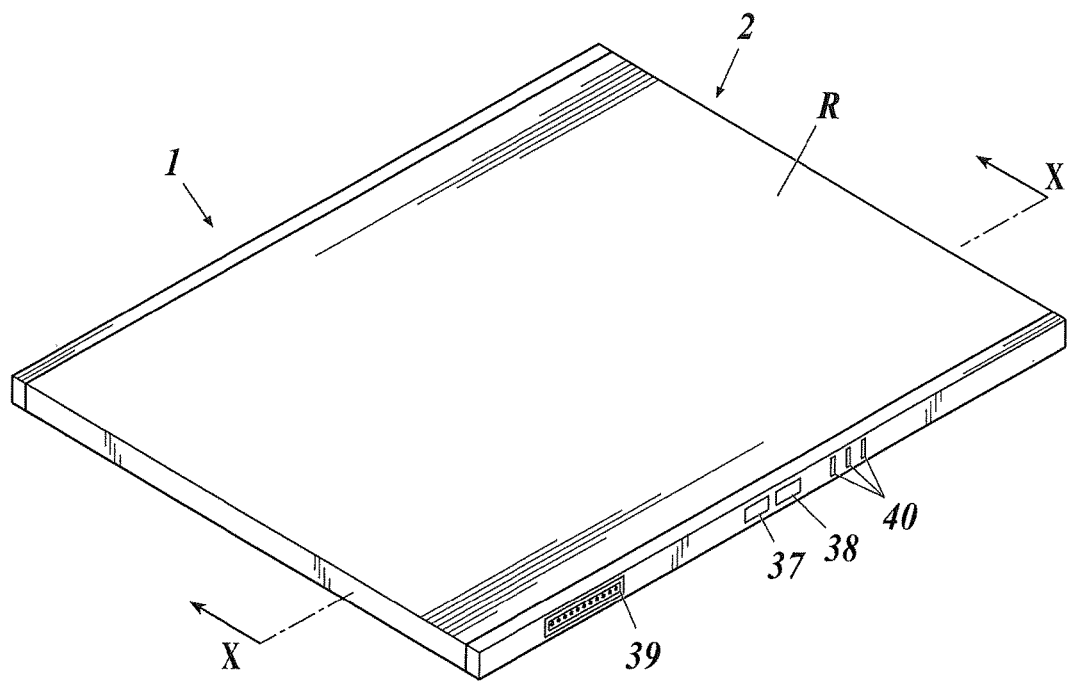
FIG. 1 is a perspective view of an outer appearance of a radiographic image capturing apparatus according to this embodiment.
Figure 2:
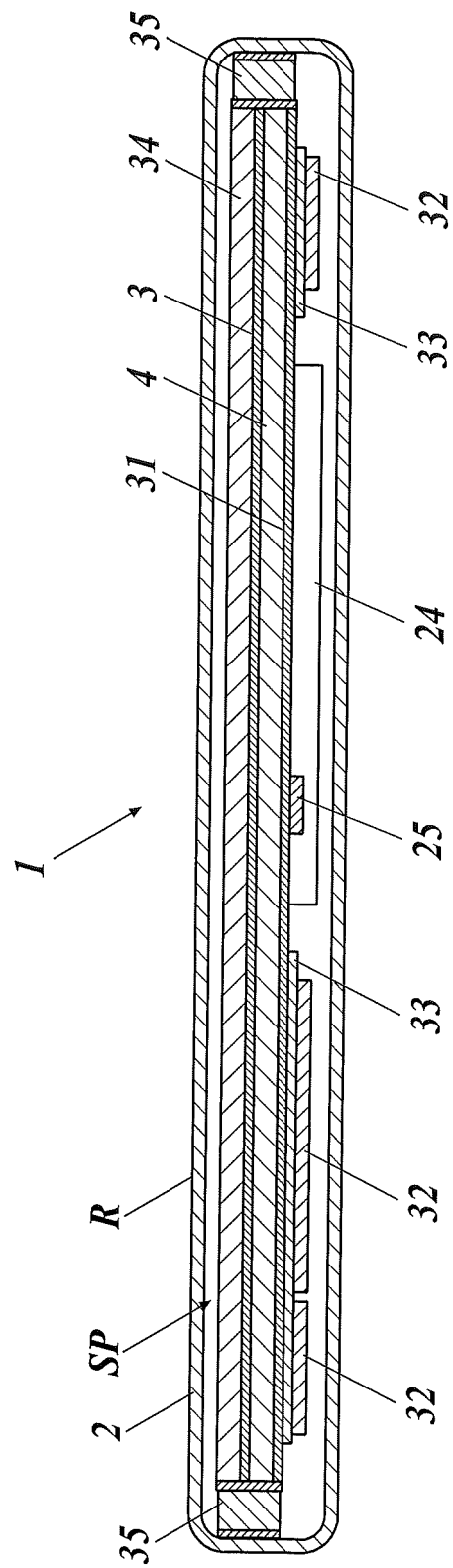
FIG. 2 is a cross-sectional view of a radiographic image capturing apparatus taken along the line X-X in FIG. 1.

The configuration of the radiographic image capturing apparatus according to this embodiment will now be described. FIG. 1 is a perspective view of an outer appearance of the radiographic image capturing apparatus according to the embodiment. FIG. 2 is a cross-sectional view of the radiographic image capturing apparatus taken along the line X-X in FIG. 1. The following description is based on the assumption that the vertical direction of the radiographic image capturing apparatus 1 is as illustrated in FIG. 2. In other words, the upper face of the radiographic image capturing apparatus 1 is a surface R on which radiation is applied and through which the radiation enters.

With reference to FIG. 1, the radiographic image capturing apparatus 1 has a housing 2 that includes a power switch 37, a changing-over switch 38, a connector 39, an indicator 40, and any other component on one side face. The housing 2 further includes an antenna 41 (not shown, refer to FIG. 4 described below) for establishing wireless communication with an external device on the opposite side face.

With reference to FIG. 2, a base 31 is disposed in the housing 2. A thin lead plate (not shown) is disposed on the base 31, and a sensor board 4 is disposed on the thin lead plate. Radiation detecting elements 7 (described below) are disposed on the sensor board 4. A scintillator 3 is formed on a scintillator board 34. The scintillator 3 and the scintillator board 34 are disposed above the sensor board 4 so that the scintillator 3 faces the radiation detecting elements 7 formed on the sensor board 4.

A printed circuit board (PCB) 33 and a built-in power supply 24 are disposed on the bottom of the base 31. The PCB 33 is provided with electronic components 32. In this embodiment, these components constitute a sensor panel SP.

A bumper 35 for the sensor panel SP is disposed between each of the longitudinal ends of the sensor panel SP and the corresponding side face of the housing 2.

Figure 3:
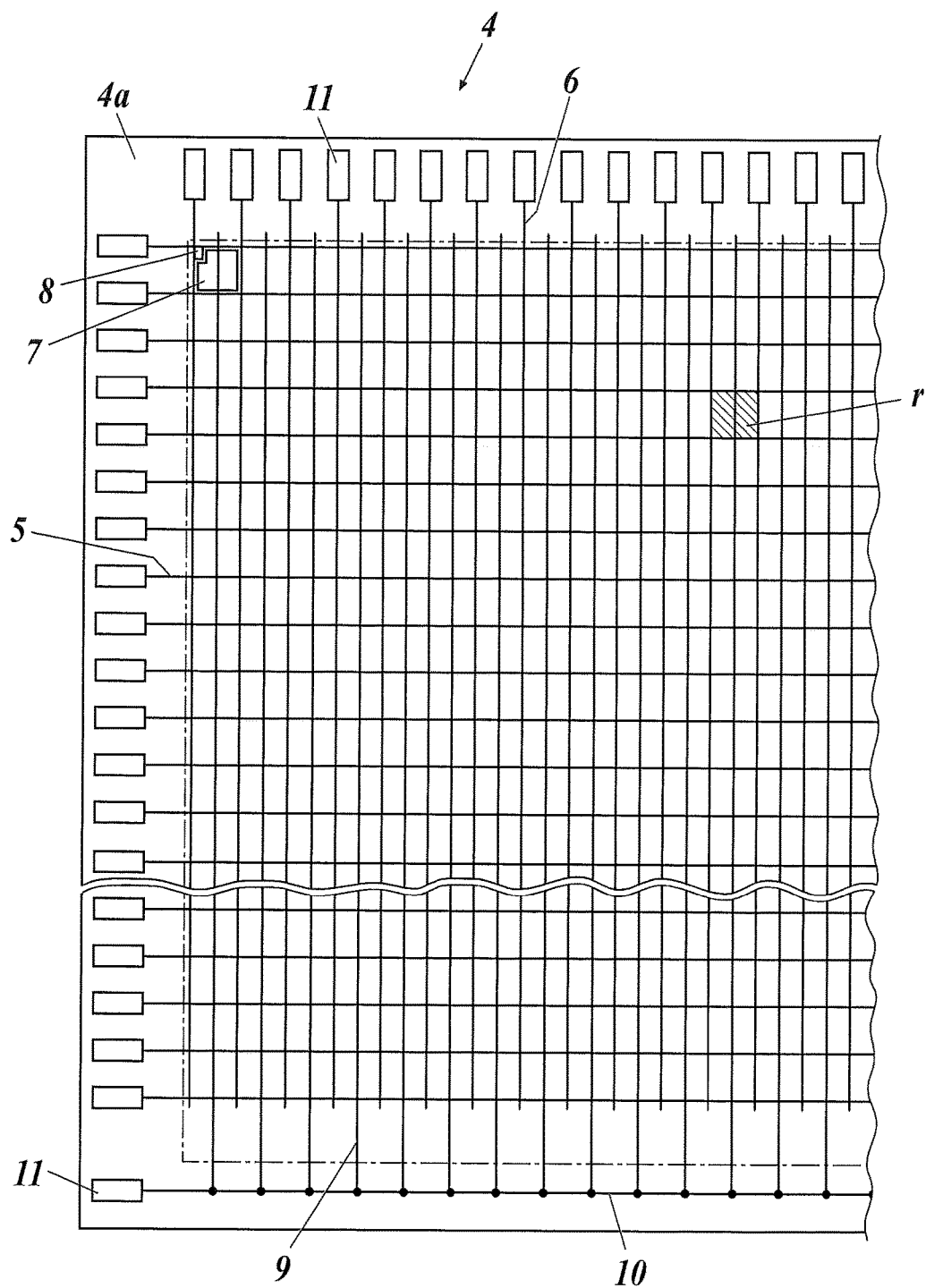
FIG. 3 is a plan view illustrating a configuration of a sensor board in the radiographic image capturing apparatus.

With reference to FIG. 3, multiple scanning lines 5 and multiple signal lines 6 intersecting with the scanning lines 5 are disposed on the upper face 4a of the sensor board 4. The upper face 4a faces the scintillator 3. Regions r defined by the scanning lines 5 and the signal lines 6 are provided with radiation detecting elements 7. In this embodiment, the radiation detecting elements 7 are disposed in a two-dimensional array (matrix).

In this embodiment, multiple bias lines 9 extend parallel to the signal lines 6 and are connected to an interconnection 10. The sensor board 4 is provided with multiple I/O terminals 11 in the periphery thereof. The I/O terminals 11 are connected to the respective scanning line 5, the respective signal lines 6 and the interconnection 10. The I/O terminals 11 are connected to a flexible circuit board (not shown) having chips, such as readout ICs 16 (described below), disposed on a film. The flexible circuit board is connected to the PCB 33 at the rear face of the sensor board 4.

Figure 4:
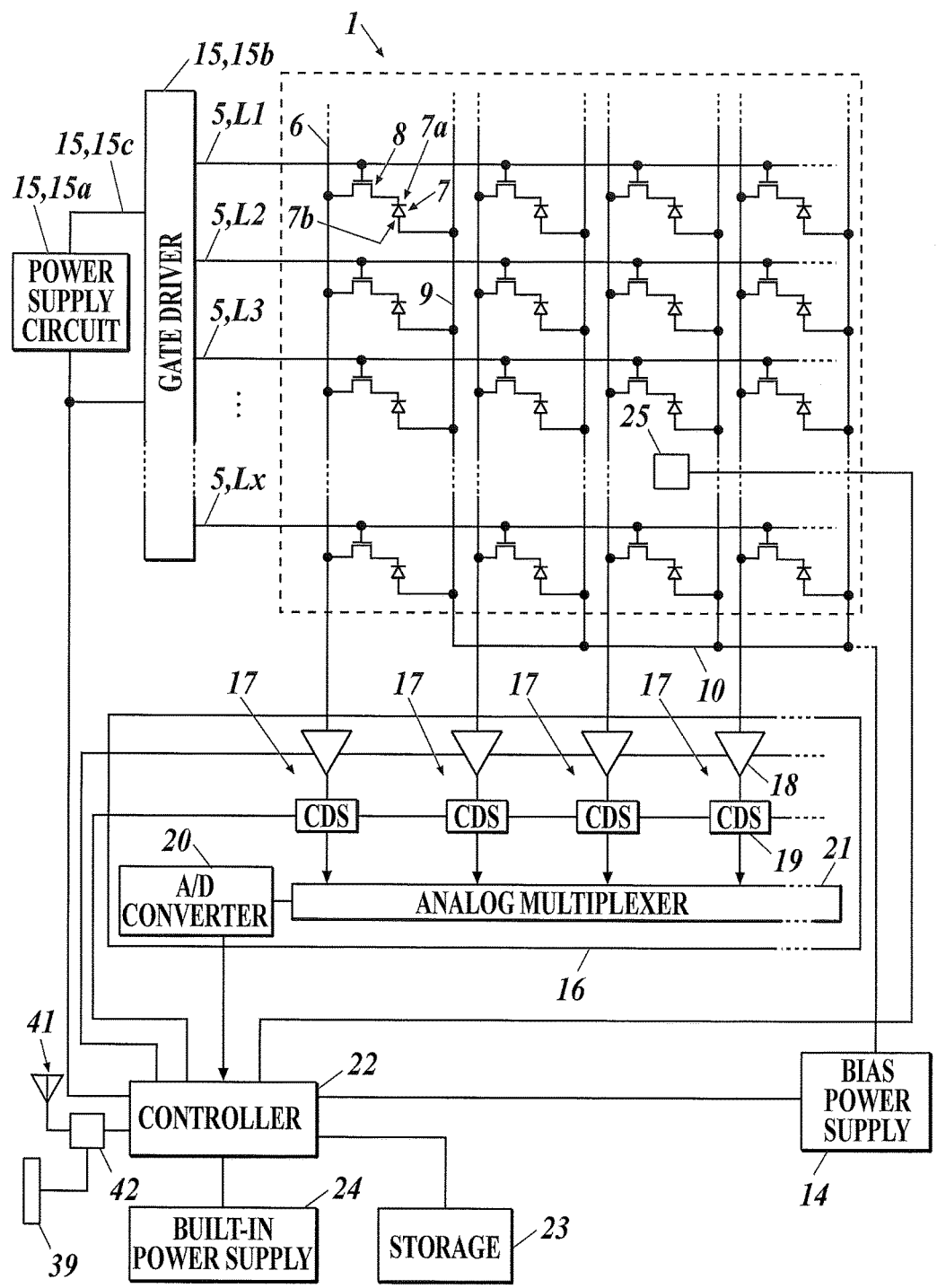
FIG. 4 is a block diagram illustrating an equivalent circuit of the radiographic image capturing apparatus.
Figure 5:
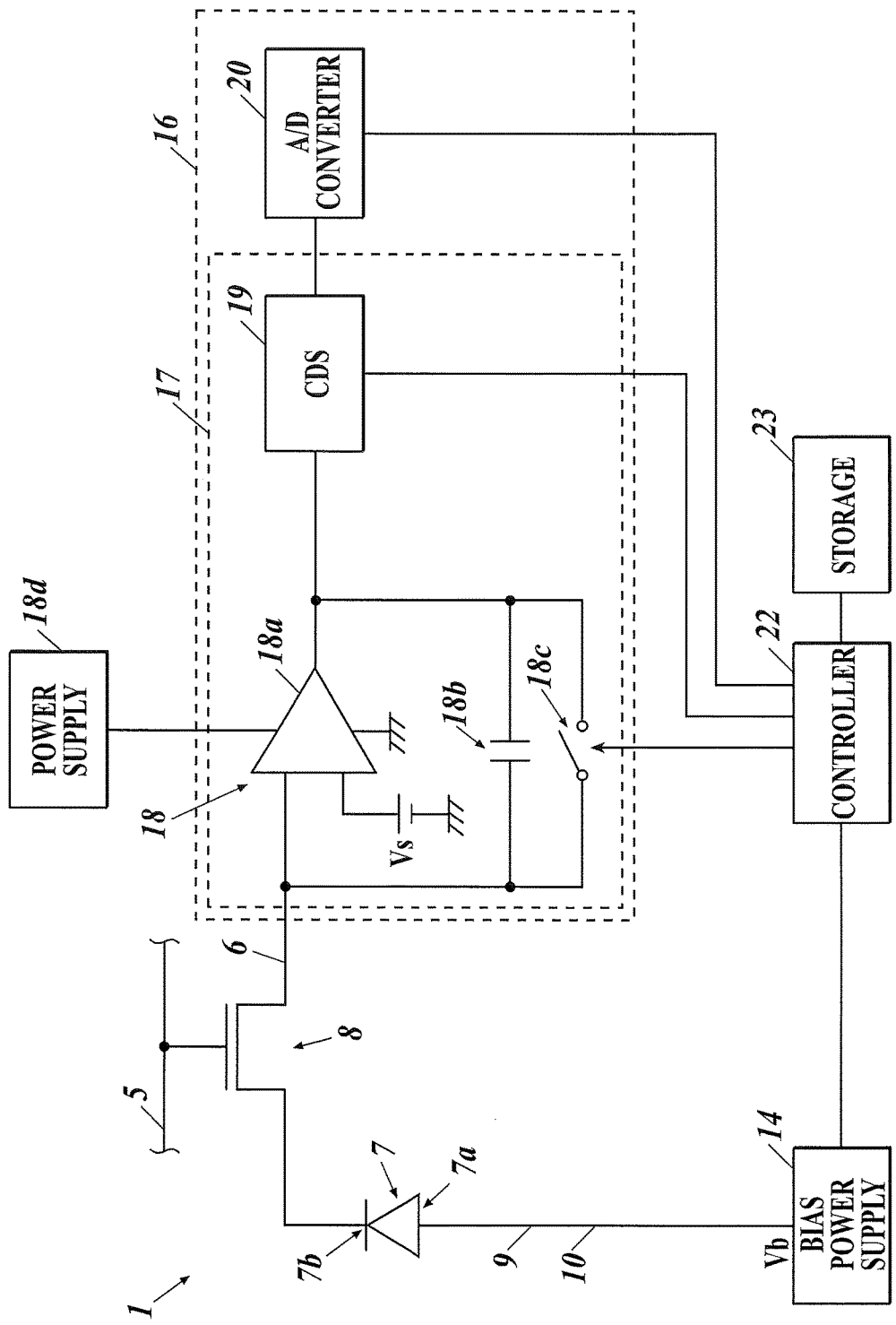
FIG. 5 is a block diagram illustrating an equivalent circuit of a radiation detecting element.

A circuit configuration of the radiographic image capturing apparatus 1 will now be described. FIG. 4 is a block diagram illustrating an equivalent circuit of the radiographic image capturing apparatus 1. FIG. 5 is a block diagram illustrating an equivalent circuit for a radiation detecting element 7 (i.e., for one pixel).

The radiation detecting elements 7 generate electric charges therein in proportion to the dose of radiation passing through a subject (not shown) or the light intensity of electromagnetic waves converted by the scintillator 3. In the following description, the radiation detecting elements 7 are photodiodes. Alternatively, the radiation detecting elements 7 may be photo-transistors or charge coupled devices (CCDs).

Each radiation detecting element 7 has an electrode 7a at one end. The electrodes 7a are connected to the respective bias lines 9. A reverse bias voltage Vb is applied from a bias power supply 14 via the bias lines 9 and the interconnection 10 to the radiation detecting elements 7. Each radiation detecting element 7 has an electrode 7b at the other end. The electrodes 7b are connected to the respective TFTs 8. The TFTs 8 function as switching elements and are connected to the respective signal lines 6.

An on-voltage is applied from a scan driving unit 15 (described below) via the scanning lines 5 to turn on the TFTs 8 to the TFTs 8, and thereby the accumulated electric charges are released from the radiation detecting elements 7 to the signal lines 6. An off-voltage is applied via the scanning lines 5 to the TFTs 8 to turn off the TFTs 8, and thereby the release of the electric charges from the radiation detecting elements 7 to the signal lines 6 is stopped and electric charges are accumulated in the radiation detecting elements 7.

The scanning lines 5 are connected to a gate driver 15b of the scan driving unit 15. The scan driving unit 15 applies an on-voltage or off-voltage from a power circuit 15a to the gate driver 15b via a line 15c. The gate driver 15b can switch a voltage to be applied to the scanning lines 5(L1) to 5(Lx) between on-voltage and off-voltage.

The signal lines 6 are connected to respective readout circuits 17 in the readout IC 16. Each readout circuit 17 in this embodiment includes an integrating circuit 18 for converting electric charges into a voltage and a correlated double sampling circuit 19. The readout IC 16 further includes an analog multiplexer 21 and an A/D converter 20. In FIGS. 4 and 5, the correlated double sampling circuits 19 are indicated by "CDS".

Each integrating circuit 18 in this embodiment includes an operational amplifier 18*a* having an inverted input terminal and an output terminal, a capacitor 18*b* and an electric charge resetting switch 18*c* that are disposed between the inverted input terminal and the output terminal of the operational amplifier 18*a*, and a charge amplifying circuit provided with a power supply 18*d* for feeding power to the operational amplifier 18*a*. The inverted input terminal of the operational amplifier 18*a* in each integrating circuit 18 is connected to the signal line 6. A reference voltage is applied to the non-inverted input terminal of the operational amplifier 18*a*.

The reference voltage applied to each signal line 6 is referred to as a "signal line voltage Vs". The electric charge resetting switch 18*c* in the integrating circuit 18 is turned on or off by a controller 22.

Upon application of radiation from the radiation emitting apparatus (not shown) to the radiographic image capturing apparatus 1 during a capturing operation while the TFTs 8 (switching elements) are in the off-state, electric charges generated in the radiation detecting elements 7 are accumulated in the radiation detecting elements 7.

During reading of image data items D from each radiation detecting element 7, the electric charge resetting switch 18*c* in the integrating circuit 18 is turned off to get the integrating circuit 18 ready for converting input electric charges into an output voltage. The correlated double sampling circuit 19 then performs a sample-and-hold operation on the reference side. An on-voltage is applied to target TFTs 8 of the radiation detecting elements 7 along one or more gate lines to release electric charges from the radiation detecting elements 7. The released electric charges are converted into a voltage at the integrating circuit 18. An off-voltage is applied to the read TFTs 8 to stop the release of electric charges. The correlated double sampling circuit 19 performs a sample-and-hold operation on the signal side, calculates a difference between the sample-and-hold operation on the signal side and the sample-and-hold operation on the reference side. The difference is converted into a digital signal at the A/D converter and then output. This operation is sequentially repeated to generate image data.

In more detail, the resetting process involves application of an initial electric charge to each radiation detecting element 7 to remove the electric charge in proportion to the dose of emitted radiation (or light intensity). The subsequent reading process involves calculation of supply electric charge required to restore the electric charge removed by the application of the initial electric charge and conversion of the calculated electric charge into a signal.

The controller 22 includes a computer having a bus connected to a central processing unit (CPU), a read-only memory (ROM), a random-access memory (RAM), and an input-output interface, a field programmable gate array (FPGA), a microcomputer, and any other components (that are not shown). The controller 22 may be a dedicated controlling circuit.

The controller 22 is connected to the storage 23, which may be a static RAM (SRAM), a synchronous DRAM (SDRAM), or a NAND flash memory, and a built-in power supply 24, which may be a lithium ion capacitor. The controller 22 is also connected to a communication unit 42 for communicating with an external device through a wireless or wired network via the antenna 41 or the connector 39.

As described above, the controller 22 controls the application of a reverse bias voltage Vb from the bias power supply 14 to the radiation detecting elements 7 and the operations of the scan driving unit 15 and the readout circuits 17, so that the image data items D are read from the radiation detecting elements 7.

Figure 6:
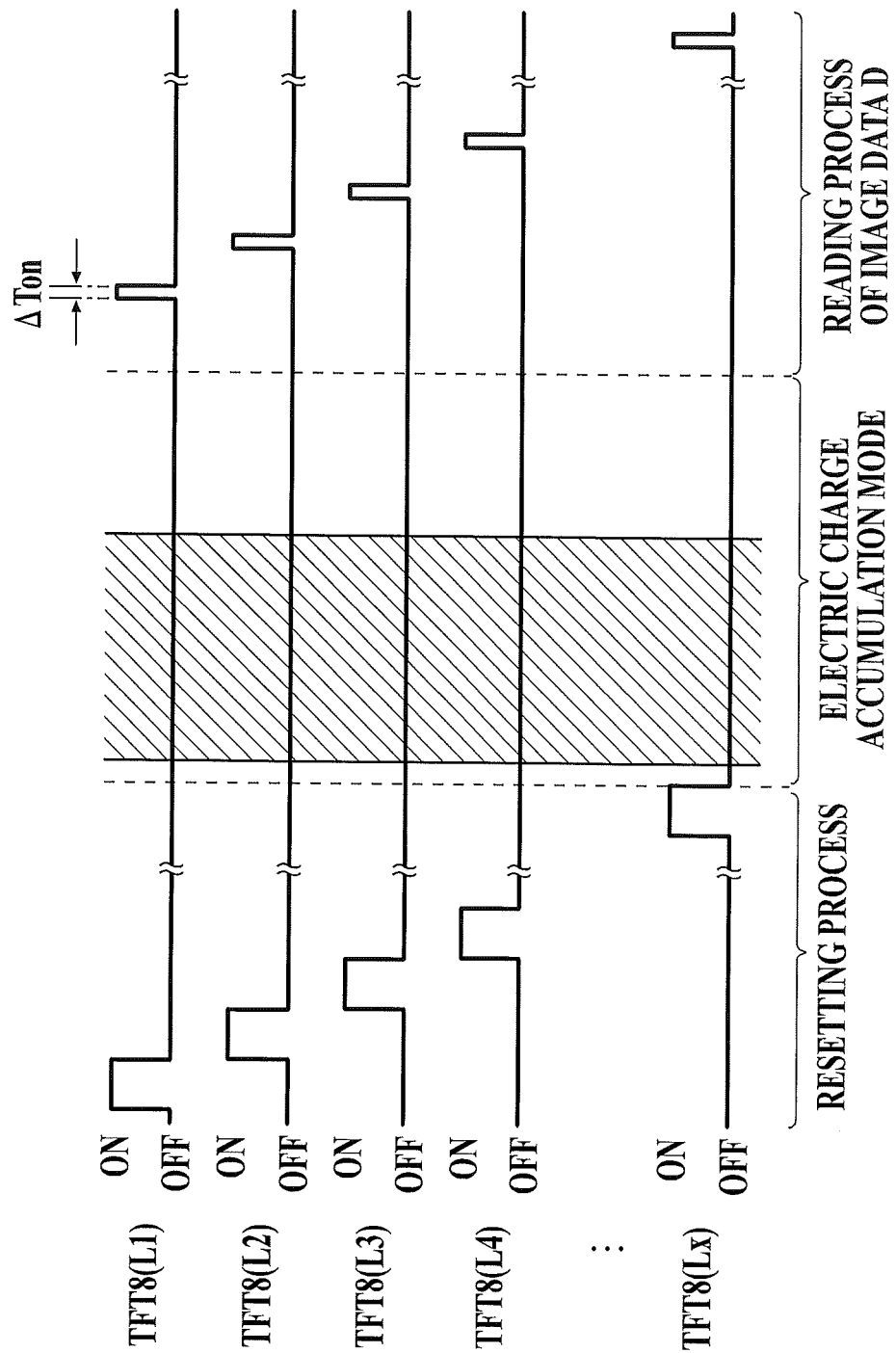
FIG. 6 is a timing chart for illustrating timing of application of an on-voltage to each scanning line during a reading process of image data.

In detail, with reference to FIG. 6, the controller 22 resets the radiation detecting elements 7 during a capturing operation: The controller 22 instructs the gate driver 15*b* of the scan driving unit 15 to sequentially apply an on-voltage to the scanning lines 5(L1) to 5(Lx) to remove electric charge remaining in each radiation detecting element 7. In more detail, the controller 22 instructs the gate driver 15*b* to apply an on-voltage to the scanning line 5(L1) to reset or remove electric charge from the scanning line 5(L1) and then to apply an off-voltage to the scanning line 5(L1). Likewise, the controller 22 then instructs the gate driver 15*b* to apply an on-voltage to the scanning line 5(L2) to reset or remove electric charge from the scanning line 5(L2) and then to apply an off-voltage to the scanning line 5(L2). The controller 22 repeats the process until all the gate lines are reset. Alternatively, the controller 22 may sequentially reset the gate lines by applying an on-voltage to the gate line L1, to the lines L1 and L2, and to the lines L1 to Lx and then applying an off-voltage to the line L1, to the lines L1 and L2, and to the lines L1 to Lx.

The controller 22 instructs the gate driver 15*b* to apply an off-voltage to the scanning lines 5(L1) to 5(Lx) to turn off the TFTs 8, and thereby the radiation detecting elements 7 transit to the electric charge accumulation mode involving accumulation of electric charges generated in the radiation detecting elements 7 by application of radiation. The hatched region in FIG. 6 indicates a period of the application of radiation to the radiographic image capturing apparatus 1.

At the end of the application of radiation, the controller 22 controls the readout unit and the scanning unit to read image data items D. The controller 22 turns off the electric charge resetting switch 18*c* of the integrating circuit 18 and instructs the correlated double sampling circuit 19 to perform a sample-and-hold operation on the reference side. The controller 22 then instructs the gate driver 15*b* to apply an on-voltage to the scanning line 5(L1) for a predetermined on-time ΔTon and then applies an off-voltage to the scanning line 5(L1). The controller 22 then instructs the correlated double sampling circuit 19 to perform a sample-and-hold operation on the signal side. The controller 22 calculates a difference between the signal side sample-and-hold operation and the reference side sample-and-hold operation. The controller 22 then instructs the A/D converter to convert the difference into an image data item D. This process is repeated for each of the scanning line 5(L1) to 5(Lx).

The controller 22 reads image data items D from the radiation detecting elements 7 during such a capturing sequence. The controller 22 stores the read image data items D in the storage 23 or transfers the stored image data items D to an external device via the communication unit 42.

In the following description, the term "on-time ΔTon" of each TFT 8 refers to a period of the application of an on-voltage to each of the scanning lines 5 (L1) to 5 (Lx) in the reading process of image data items D, in other words, a period between the switch from an off-voltage application to an on-voltage application to the scanning lines 5 (L1) to 5 (Lx) and the switch from the on-voltage application to an off-voltage application to the scanning lines 5(L1) to 5(Lx) (refer to on-time ΔTon in FIG. 6).

The controller 22 according to this embodiment controls the reading process of image data items D from the radiation detecting elements 7 in accordance with an ongoing capturing sequence. If the capturing sequence is a still-image capturing sequence, the controller 22 resets the radiation detecting elements 7 and performs a procedure involving accumulating electric charge, applying radiation, and reading image data items D, as shown in FIG. 6. In this case, each operation in the procedure is performed once.

In contrast, if the preset capturing sequence is a dynamic image capturing sequence, the controller 22 resets the radiation detecting elements 7 and repeats the cycle involving accumulating electric charge, applying radiation, and reading image data items D (in the order of resetting the radiation detecting elements, accumulating electric charge, applying radiation, reading image data items D, accumulating electric charge, applying radiation, reading image data items D, . . . ), as shown in FIG. 6.

For dynamic image capturing involving pulsed radiation application, the controller 22 repeats the cycle described above. For dynamic image capturing involving a sequential radiation application, the controller 22 may repeat the cycle involving accumulating electric charge and reading image data items D (in the order of accumulating electric charge, reading image data items D, accumulating electric charge, reading image data items D, . . . ) during radiation application.

Different capturing sequences have different number of reading operations, different on-times ΔTon of the TFTs 8, different parameters and procedures. For example, the dynamic image capturing sequence has a shorter on-time ΔTon of each TFT 8 than that for the still-image capturing sequence.

With reference to FIG. 2, the radiographic image capturing apparatus 1 according to this embodiment is provided with a temperature sensor 25 on the rear face of the base 31 to measure the temperature in the radiographic image capturing apparatus 1. With reference to FIG. 4, the temperature sensor 25 is connected to the controller 22 so as to transfer information on the temperature measured in the radiographic image capturing apparatus 1 to the controller 22. The radiographic image capturing apparatus 1 does not necessarily include a temperature measuring unit, such as the temperature sensor 25.

[Radiological Image Capturing System]

Figure 7:
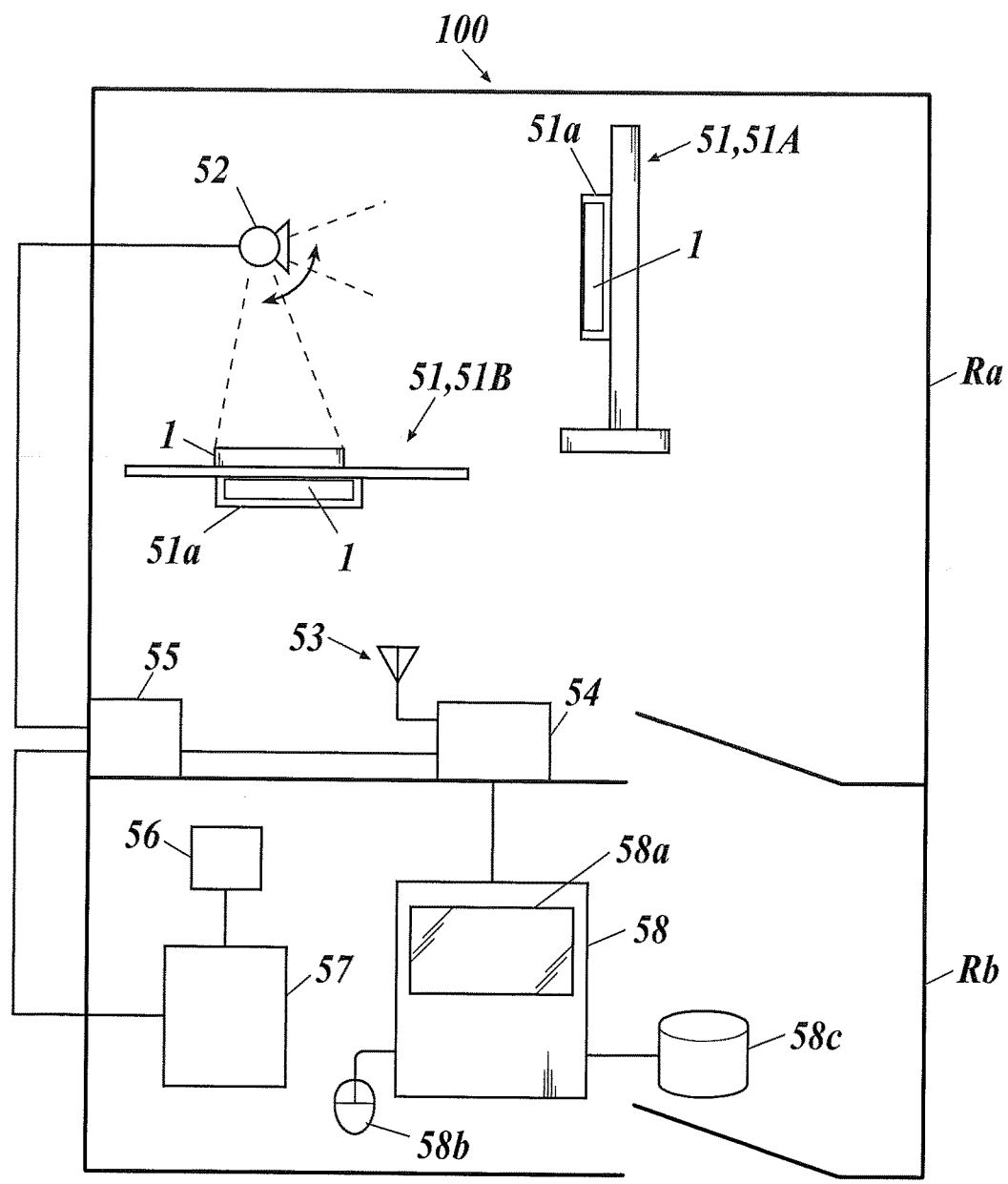
FIG. 7 illustrates an exemplary configuration of a radiographic image capturing system according to this embodiment.
Figure 8:
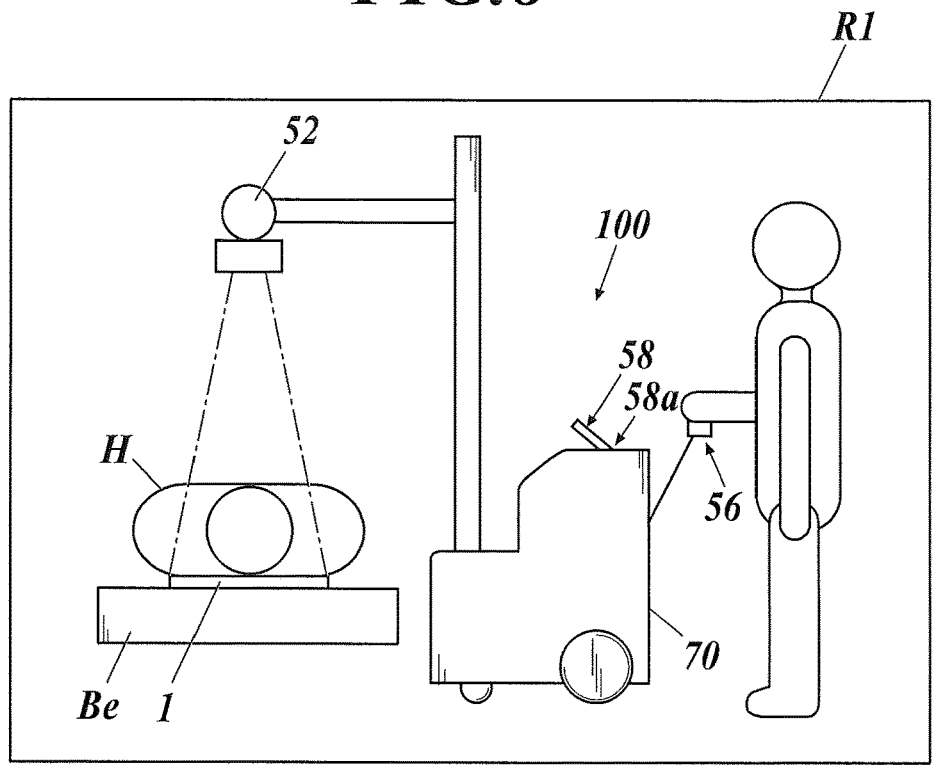
FIG. 8 illustrates another configuration of the radiographic image capturing system according to this embodiment.

A radiographic image capturing system according to this embodiment will now be described. The radiographic image capturing system 100 may be installed in, for example, a capturing chamber Ra or a front chamber Rb, as shown in FIG. 7. Alternatively, the radiographic image capturing system 100 may be installed in a medical cart 70, as shown in FIG. 8.

For the radiographic image capturing system 100 installed in the capturing chamber Ra, the radiographic image capturing apparatus 1 may be placed in, for example, a cassette holder 51*a* of a capturing platform 51, as shown in FIG. 7. The capturing platform 51A is a standing radiographic capturing stand, and the capturing platform 51B is a supine radiographic capturing stand. Alternatively, the radiographic image capturing apparatus 1 may be placed, for example, between a subject (not shown) lying on a top panel of the capturing platform 51B and the top panel.

The capturing chamber Ra is provided with at least one radiation generating device 52, which emits radiation. The capturing chamber Ra is also provided with a repeater 54 having an access point 53. The access point 53 relays communications between devices inside and outside the capturing chamber Ra through a wireless or wired network. The repeater 54 is connected to the generator 55 of the radiation generating device 52 and a console 58 and relays communications among the radiographic image capturing apparatus 1, the console 58, and the generator 55 of the radiation generating device 52.

The generator 55 of the radiation generating device 52 conducts various controlling operations of the radiation generating device 52. For example, the generator 55 instructs the radiation generating device 52 to emit radiation in a dose in proportion to an X-ray tube voltage, an X-ray tube current, or irradiation time (or mAs value) determined by an operator or radiological technician.

The front chamber Rb (also referred to as an operation room) is provided with a console 57 of the radiation generating device 52. The console 57 is provided with an exposure switch 56 which is manipulated by an operator, such as a radiological technician, to instruct the generator 55 to start emitting radiation. The front chamber Rb is also provided with the console 58 with a built-in computer. The console 58 may be installed outside the capturing chamber Ra and front chamber Rb or inside any other chamber.

The console 58 is provided with a display 58*a* of a cathode ray tube (CRT) or liquid crystal display (LCD) and is connected to an input device 58*b*, such as a mouse or a keyboard. The console 58 is also connected to or includes a storage unit 58*c*, which may be a hard disk drive (HDD).

As described above, the radiographic image capturing system 100 equipped with the radiation generating device 52 and the console 58 may be included in the medical cart 70, as shown in FIG. 8. The medical cart 70 may be moved to a medical ward R1 for a capturing operation. In this case, the generator 55 of the radiation generating device 52 and the repeater 54 (not shown) are included in the medical cart 70.

In this case, the radiographic image capturing apparatus 1 is placed between a bed Be and a subject (patient) H, as shown in FIG. 8, or is placed on the body of the patient to perform capturing. An operator, such as a radiological technician, turns on the exposure switch 56 to cause the radiation generating device 52 to emit radiation for image capturing.

Figure 9:
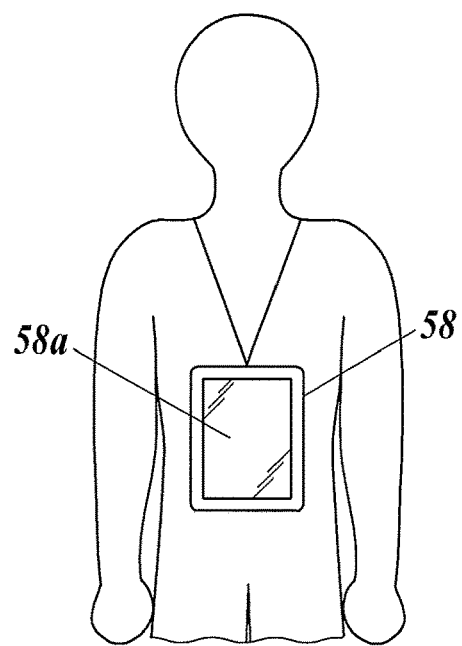
FIG. 9 illustrates an exemplary configuration of a portable console.

The console 58 may be a desk-top or lap-top computer, as shown in FIGS. 7 and 8. Alternatively, the console 58 may be a mobile terminal carried by the operator, such as a radiological technician, as shown in FIG. 9.

[Radiographic Image Generation Process in Image Processor]

Upon reading of image data items D from the radiation detecting elements 7, as described above, the radiographic image capturing apparatus 1 of the radiographic image capturing system 100 according to this embodiment sends the image data items D to the console 58. The console 58 generates radiographic images based on the image data items D.

The console 58 according to this embodiment functions as an image processor that generates radiographic images based on the image data items D. In the following description, the console 58 functioning as an image processor is referred to as an "image processor 58". In another embodiment, the image processor may be a component separated from the console 58. The image processor may perform part of or the entire image processing (image correction) in the FPD.

[Cause of Uneven Image Density of Corrected Image Data]

Figure 17A:
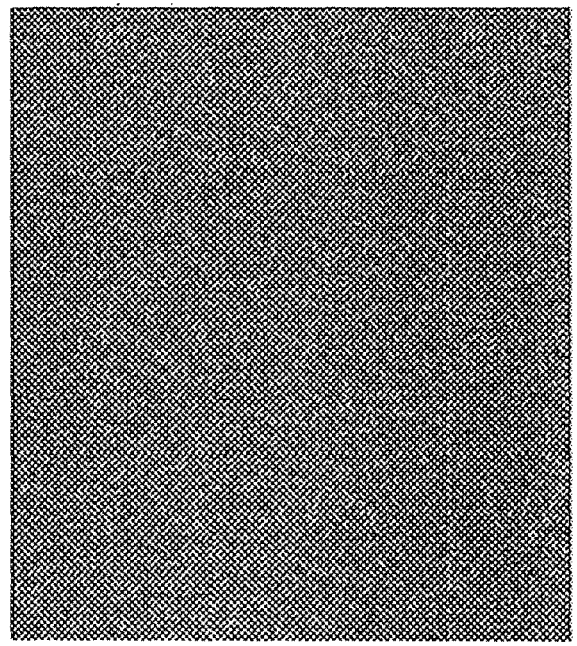
FIG. 17A is a photographic image including corrected image data items having an identical value.
Figure 17B:
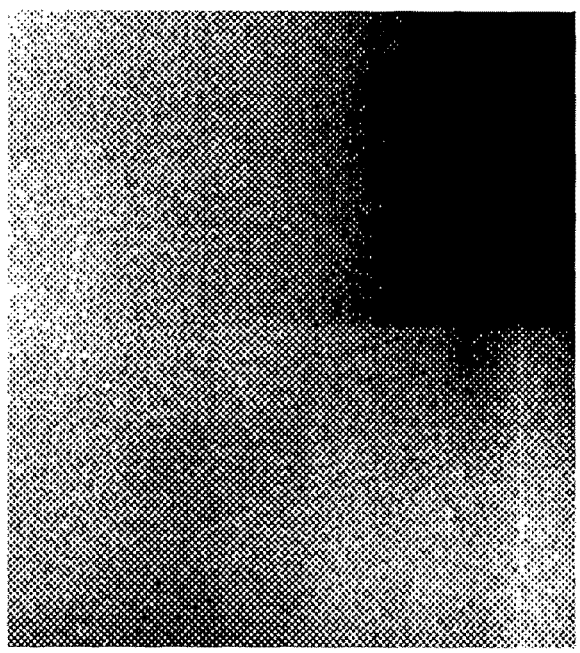
FIG. 17B is a photographic image including corrected image data items having uneven image density.

Now described is the cause of uneven image density of a corrected image data item D* shown in FIG. 17B.

For example, image data items D are read through the still-image capturing sequence (refer to FIG. 6) with the radiographic image capturing apparatus 1, and gain data a is calculated based on the image data items D. The gain data a is then applied to the image data items D for one frame read through a capturing sequence (for example, a dynamic image capturing sequence) other than the still-image capturing sequence with the radiographic image capturing apparatus 1 to correct the image data items D in accordance with the above Expression (1). As shown in FIG. 17B, the corrected image data item D* may have errors or uneven image density.

The inventors of the present invention have investigated the cause of this phenomenon and found that a reduction in the on-time ΔTon of each TFT 8 in a capturing sequence of the radiographic image capturing apparatus 1 causes a variation in the readout efficiencies Ero among the radiation detecting elements 7 and that the variation in the readout efficiencies Ero are different in each radiation detecting element 7, leading to uneven image density.

In more detail, the following expression holds true:

Image data item $D \approx S \times \{1-\exp(-\Delta Ton/\tau)\}$ (2)

$\tau \approx C \times Ron$ (3)

where "C" represents a capacity (stray capacity) of each radiation detecting element 7, "Ron" represents an equivalent resistance of the switching element TFT in the on-state, which varies depending on temperature, "S" represents a signal value accumulated in the radiation detecting element 7, and "τ" represents a time constant.

In this case, the readout efficiency is determined by the following expression:

$Ero \approx 1-\exp(-\Delta Ton/\tau)$ (4)

C and Ron vary depending on the radiation detecting elements 7.

Figures 10, 11:
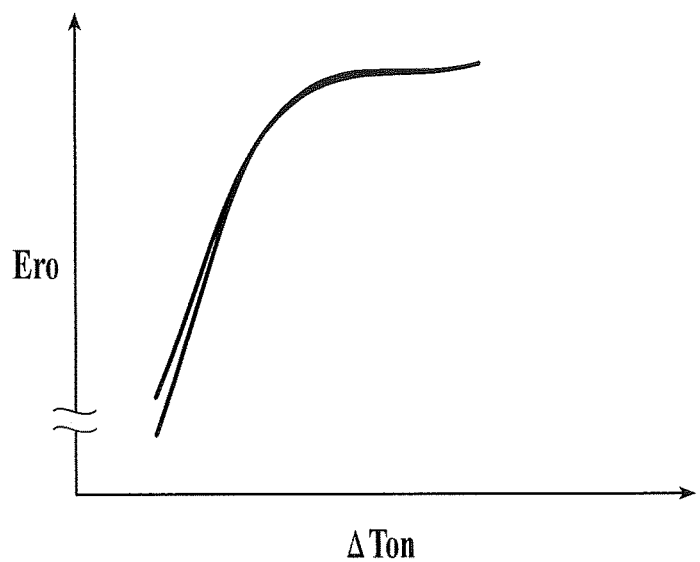
FIG. 10 is a graphical representation of a difference in dependency of a readout efficiency Ero read from each radiation detecting element on an on-time $\Delta Ton$.
FIG. 11 is a table illustrating reference gain data and offset data that are preliminarily stored in an image processor and are used to correct the gains of the radiation detecting elements.

More specifically, different capturing sequences of the radiographic image capturing apparatus 1 have different on-times ΔTon of the TFTs 8 (refer to FIG. 6) for reading image data items D. This causes a variation in the readout efficiencies Ero among the radiation detecting elements 7. The inventors of the present invention investigated how the readout efficiencies Ero of the radiation detecting elements 7 vary in response to the variation in the on-times ΔTon of the TFTs 8. The investigation reveals that a longer on-time ΔTon of each TFT 8 leads to a higher readout efficiency Ero of each radiation detecting element 7, as shown in FIG. 10. In other words, longer opening of the switching element increases electric charge released from each radiation detecting element 7 to the corresponding signal line 6.

A sufficiently long on-time ΔTon of each TFT 8 allows release of the electric charge in a sufficient amount from each radiation detecting element 7 to the corresponding signal line 6 via the corresponding TFT 8. This causes each radiation detecting element 7 to have readout efficiency Ero of approximately 100%, with substantially no difference in the readout efficiencies Ero among the radiation detecting elements 7. For example, an on-time ΔTon equal to at least six times the time constant T leads to a readout efficiency Ero of approximately 100%. A shorter on-time ΔTon of each TFT 8 causes a difference in amount of the electric charge passing through each TFT 8, resulting in a difference in the readout efficiencies Ero among the radiation detecting elements 7.

Although FIG. 10 shows the dependency relations of the readout efficiencies Ero on the on-times ΔTon only for two radiation detecting elements 7 (or TFTs 8), different radiation detecting elements 7 (or TFTs 8) have different dependency relations. As described above, the radiographic image capturing apparatus 1 operating in a videographic capturing sequence inevitably has a shorter on-time ΔTon of each TFT 8 during the reading of image data item D to achieve a high frame rate.

In some cases, the radiographic image capturing apparatus 1 determines different on-times ΔTon of the TFTs 8 depending on the type of videographic capturing sequences, such as normal videographic capturing, dynamic image capturing, tomosynthesis, and dual energy subtraction.

For example, if image data items D are read through a still-image capturing sequence having a sufficiently long on-time ΔTon of each TFT 8 with the radiographic image capturing apparatus 1 and gain data a is determined based on the image data items D, the readout efficiency Ero of each radiation detecting element 7 has approximately 100% with substantially no difference among the radiation detecting elements 7, as shown in FIG. 10.

If the image data item D is read through, for example, a dynamic image capturing sequence having a short on-time ΔTon of each TFT 8 with the radiographic image capturing apparatus 1, a difference is caused in the readout efficiencies Ero among the radiation detecting elements 7. In other words, even if the radiation detecting elements 7 accumulate the same amount of electric charge, a variation is caused in the values of the image data items D; the image data item D read from a radiation detecting element 7 with a high readout efficiency Ero has a relatively large value, whereas the image data item D read from a radiation detecting element 7 with a low readout efficiency Ero has a relatively small value.

The application of the gain data a determined based on the image data items D read through the still-image capturing sequence with the radiographic image capturing apparatus 1 to the image data items D read through the dynamic image capturing sequence for gain correction cannot properly correct the difference in the values of the image data items D due to the difference in the readout efficiencies Ero among the radiation detecting elements 7 (refer to FIG. 10). Uncorrected differences remain in the corrected image data item D*.

The radiographic image generated under such conditions has a portion including the corrected image data items D* with a relatively large value (i.e., an area including TFTs 8 with a relatively high readout efficiency Ero) and a portion including the corrected image data items D* with a relatively small value (i.e., an area including TFTs 8 with a relatively low readout efficiency Ero). The difference between the two portions is visibly observed as uneven image density.

As described above, before the factory shipment, if the image data items D captured through a videographic capturing sequence having a short on-time ΔTon at a temperature T0 are corrected with gain data a' determined based on the image data items D captured through the videographic capturing sequence having a short on-time ΔTon at the same temperature T0, the corrected image data items D* do not have uneven image density. In contrast, if the image data items D captured at a different temperature T1 are corrected with the gain data a', the corrected image data items D* has uneven image density described above. The uneven image density is caused by a variation in the equivalent resistance Ron of the on-state TFT in the above Expression (3) depending on temperatures.

The time constant τ in $\exp\{-\Delta Ton/\tau\}$ in the Expression (2) has a temperature characteristic τ(T) as a function of temperature (T). If the on-time ΔTon is significantly (for example, at least six times) larger than τ(T), a variation in τ(T) depending on temperatures barely has any affects and causes no uneven image density.

It is demonstrated from the above phenomenon that the cause of the uneven image density of the corrected image data items D* lies in a difference in the readout efficiencies Ero among the radiation detecting elements 7. The cause of the difference in the readout efficiencies Ero lies in an on-time ΔTon shorter than the time constant T of each radiation detecting element 7 and variations in the time constant T depending on temperatures.

It is also demonstrated that the application of the gain data a determined based on image data items D read from the radiation detecting elements 7 of the radiographic image capturing apparatus 1 through a still-image capturing sequence having the on-time ΔTon of each TFT 8 significantly larger than the time constant T to the image data items D read through another capturing sequence having a relatively small on-time ΔTon with a radiographic image capturing apparatus 1 results in the difference in the readout efficiencies Ero of the radiation detecting elements 7. The corrected image data items D* have uneven image density due to the difference in the readout efficiencies Ero, unlike the corrected image data items D* obtained through the still-image capturing having a read-out efficiency of approximately 100%.

[Configuration of the Radiographic Image Capturing System According to this Embodiment]

Determination of the gain data a for each capturing sequence of the radiographic image capturing apparatus 1 or for each temperature in the radiographic image capturing apparatus 1 leads to gain correction that does not cause uneven image density; however, such determination of the gain data a for each on-time ΔTon and for each temperature before the factory shipment is impractical because it is time consuming and requires multiple gain data to be stored. Determination of gain data a by a radiological technician before a capturing operation is also impractical because it requires a lot of efforts.

In most cases, the radiographic image capturing apparatus 1 preliminarily stores multiple gain data a for correcting the gains of the radiation detecting elements 7 (hereinafter referred to as "reference gain data ast"), as illustrated in FIG. 11. Before the factory shipment, a capturing sequence (for example, a still-image capturing sequence, refer to FIG. 6) having the on-time ΔTon significantly longer than the time constant T is performed with the radiographic image capturing apparatus 1 in consideration of variations in temperature, and the radiation incident surface R (refer to FIGS. 1 and 2) of the radiographic image capturing apparatus 1 is irradiated evenly with radiation so that the image data items D read from the radiation detecting elements 7 have an identical value. The reference gain data ast is used to correct the gain of efficiency for converting radiation from a scintillator into electromagnetic waves, such as visible light, photoelectric conversion efficiency of a photovoltaic device (radiation detecting element), and efficiency for converting electric charge signals in the readout circuits 17 into digital signals.

The offset data O in the Expression (1) for each radiation detecting element 7 can be preliminarily read and stored in the radiographic image capturing apparatus 1 before the factory shipment, as described above. For simplicity, the following description is based on the assumption that the offset data O is preliminarily read and stored in the radiographic image capturing apparatus 1 before the factory shipment; however, the offset data O may be read and determined before or after a capture operation.

With reference to FIG. 11, (x, y) represents an array of the radiation detecting elements 7 in xth line and yth row on the sensor board 4 (refer to FIG. 3). In the following description, the term "reference capturing sequence" refers to the capturing sequence of the radiographic image capturing apparatus 1 through which the reference gain data ast is determined based on the captured image data items D (i.e., the still-image capturing sequence in the above example). The following description is based on the assumption that the reference capturing sequence is the still-image capturing sequence; however, the reference capturing sequence may be any other capturing sequence.

The image processor 58 in the radiographic image capturing system 100 according to this embodiment corrects the image data item D transferred from the radiographic image capturing apparatus 1. In detail, as shown in the following Expression (5), the reference gain data ast for each radiation detecting element 7 is modified with the readout efficiency Ero of the radiation detecting element 7 corresponding to the capturing sequence of the radiographic image capturing apparatus 1 other than the reference capturing sequence and the temperature in the radiographic image capturing apparatus 1, and then the image data item D is corrected based on the offset data O and the modified reference gain data ast* (in place of the gain data a in the above Expression (1)).

$$ast^* = ast/Ero \qquad (5)$$

The image data item D is corrected in accordance with the following expression, where the gain data a in the above Expression (1) is replaced with the modified gain data ast*, to determine corrected image data item D*:

$$D^* = ast^* \times (D-O) \qquad (6)$$

The image processor 58 modifies the reference gain data ast based on the readout efficiency Ero of each radiation detecting element 7 (refer to the above Expression (5)) and corrects the image data item D transferred from the radiographic image capturing apparatus 1 based on the offset data O and the modified gain data ast* in accordance with the above Expression (6) where the gain data a in the above Expression (1) is replaced with the modified gain data ast*). The image processor 58 performs elaborate image processing on the corrected image data item D*, such as a gradation process, depending on a captured portion and generates the radiographic image.

The image processor 58 preliminarily stores the reference gain data ast and the offset data O of each radiation detecting element 7 for correcting the gain in, for example, the storage unit 58c (refer to FIG. 7, not shown in FIG. 8) for each radiographic image capturing apparatus 1 available in the radiographic image capturing system 100.

[Calculation of Readout Efficiency Ero of Radiation Detecting Element 7]

In this embodiment, the reference gain data ast for each radiation detecting element 7 is modified with the readout efficiency Ero of the radiation detecting element 7 (refer to the above Expression (5)), as described above. The readout efficiency Ero of each radiation detecting element 7 is determined for each capturing sequence of the radiographic image capturing apparatus 1 or for each temperature in the radiographic image capturing apparatus 1.

Determination of the readout efficiency Ero of each radiation detecting element 7 after the application of radiation to the radiographic image capturing apparatus 1 requires a radiological technician to conduct a very bothersome capturing operation to apply radiation. To avoid such a situation, the radiographic image capturing apparatus 1 according to this embodiment can automatically calculate the readout efficiency Ero of each radiation detecting element 7 without application of radiation, i.e., without the need for the operation by a radiological technician.

In the following description, the radiographic image capturing apparatus 1 reads and sends signal values S to the image processor 58 and the image processor 58 calculates the readout efficiency Ero of each radiation detecting element 7 of the radiographic image capturing apparatus 1; instead, the controller 22 in the radiographic image capturing apparatus 1 may calculate the readout efficiency Ero of each radiation detecting element 7 in place of the image processor 58.

[Reading Process of Signal Values in Radiographic Image Capturing Apparatus]

Figure 12:
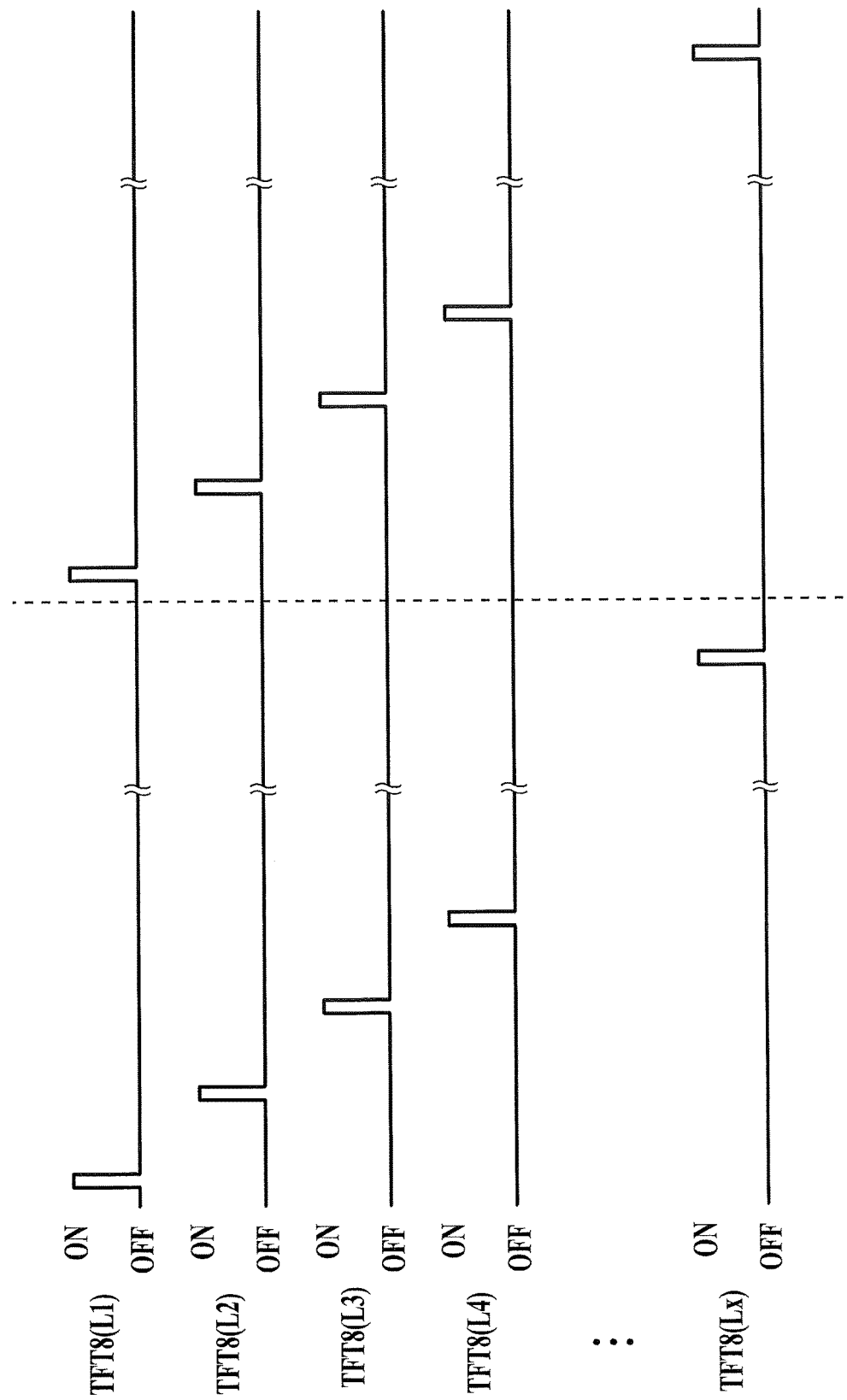
FIG. 12 is a timing chart illustrating timing of sequential application of an on-voltage to TFTs during sequential application of an on-voltage to the scanning lines to reset the radiation detecting elements.

With reference to FIG. 12, the controller 22 of the radiographic image capturing apparatus 1 resets the radiation detecting elements 7 by sequentially applying an on-voltage from the gate driver 15b of the scan driving unit 15 (see FIG. 4) to the scanning lines 5(L1) to 5(Lx) to sequentially turn on the TFTs 8. This operation releases electric charges from the radiation detecting elements 7 to the signal lines 6 to remove electric charges remaining in the radiation detecting elements 7.

Alternatively, the radiation detecting elements 7 may be reset by concurrently applying an on-voltage to the scanning lines 5(L1) to 5(Lx), instead of sequentially applying an on-voltage to the scanning lines 5(L1) to 5(Lx). The resetting process of the radiation detecting elements 7 will be described in detail. Since the purpose of the resetting process is to remove electric charges remaining in the radiation detecting elements 7, the resetting process of the radiation detecting elements 7 may be replaced with the reading process to read image data items D from the radiation detecting elements 7, for example.

Figure 13:
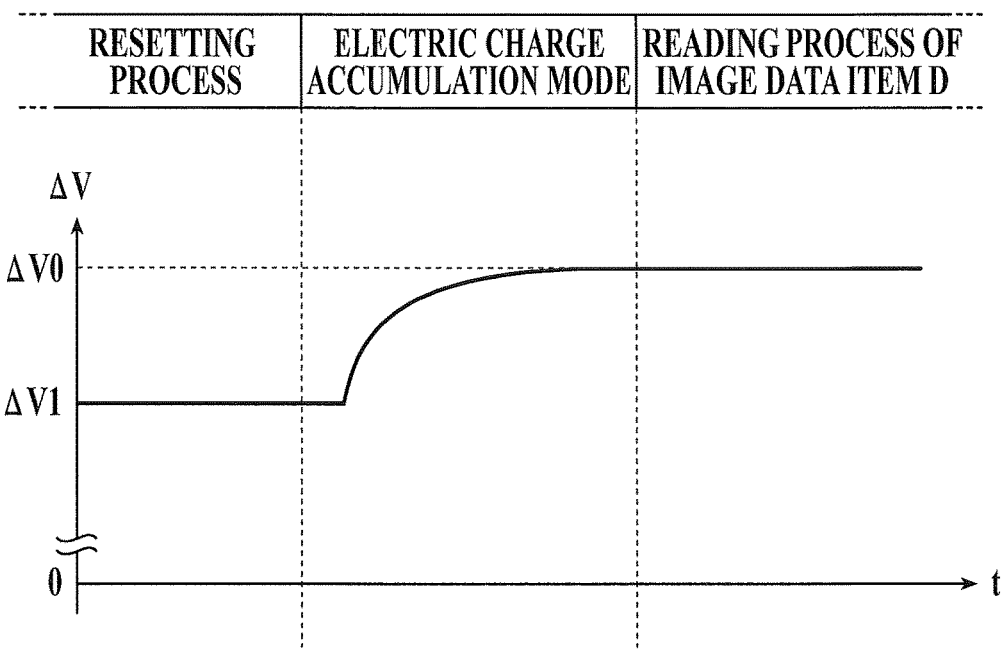
FIG. 13 is a graphical representation of a potential difference between the electrodes of a radiation detecting element during sub-processes and in a mode before a reading process of signal values in the radiographic image capturing apparatus.
Figure 14:
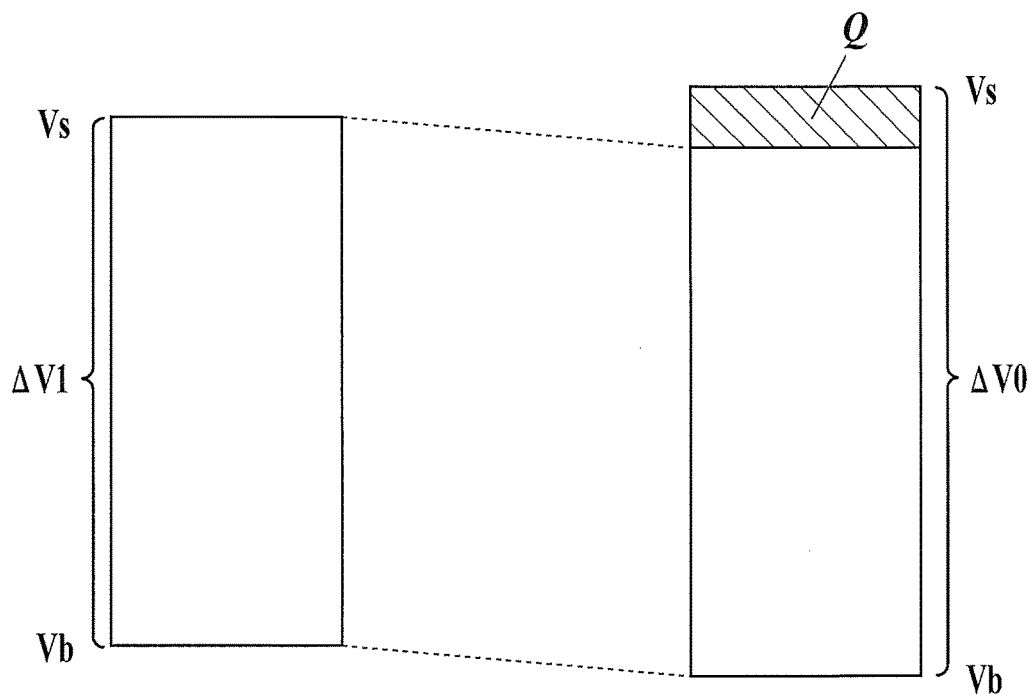
FIG. 14 illustrates the accumulation of electric charge in each radiation detecting element in response to a variation in the potential difference between the electrodes of the radiation detecting element in an electric charge accumulation mode.

If the potential difference $\Delta V0$ between the two electrodes 7a and 7b of each radiation detecting element 7 (see FIGS. 4 and 5) is, for example, 5 [V] during the reading of the image data items D from the radiation detecting elements 7 through a normal capturing operation, the controller 22 sets the potential difference $\Delta V1$ between the two electrodes 7a and 7b of each radiation detecting element 7 to an absolute value, for example, 4.5[V], smaller than the potential difference $\Delta V0$ during the resetting process of the radiation detecting elements 7, as shown in FIG. 13, to reset the radiation detecting elements 7.

As described above, the reverse bias voltage Vb is applied to the electrode 7a at one end of each radiation detecting element 7, while the signal line voltage Vs is applied to the signal line 6 connected to the electrode 7b at the other end of the radiation detecting element 7 via the corresponding switching element. The potential difference $\Delta V$ between the two electrodes 7a and 7b of each radiation detecting element 7 during the turned-on state of the TFT 8 is calculated as follows:

$$\Delta V = Vs - Vb \quad (7)$$

In this embodiment, the potential difference $\Delta V$ between the two electrodes 7a and 7b of each radiation detecting element 7 can be varied after the resetting process or the reading process by varying at least one or both of the reverse bias voltage Vb and the signal line voltage Vs. The signal line voltage Vs can be varied by varying the reference voltage applied to the non-inverted input terminal of the operational amplifier 18a (see FIG. 5) of the integrating circuit 18 in the readout circuit 17.

With reference to FIG. 13, the controller 22 resets the radiation detecting elements 7, while the potential difference between the signal line voltage Vs and the reverse bias voltage Vb is set to $\Delta V1$ (for example, 4.5[V]), so that the potential difference between the two electrodes 7a and 7b of each radiation detecting element 7 can be set to $\Delta V1$. The controller 22 instructs the gate driver 15b to apply an off-voltage to the scanning lines 5(L1) to 5(Lx) to turn off the TFTs 8. This causes the radiation detecting elements 7 to transit to the electric charge accumulation mode. During the electric charge accumulation mode, the radiographic image capturing apparatus 1 is not irradiated with radiation.

After the transition of the radiation detecting elements 7 to the electric charge accumulation mode, the controller 22 varies at least one or both of the signal line voltage Vs and the reverse bias voltage Vb such that the potential difference between the signal line voltage Vs and the reverse bias voltage Vb is changed to $\Delta V0$. The controller 22 waits for the change of the potential difference to $\Delta V0$ and then starts the reading process after the change. The potential difference $\Delta V$ between the two electrodes 7a and 7b of each radiation detecting element 7 is kept at $\Delta V1$ before the start of the reading process since the radiation detecting elements 7 are in the electric charge accumulation mode. At the start of the reading process in this mode, the potential difference $\Delta V$ between the two electrodes 7a and 7b of each radiation detecting element 7 varies from $\Delta V1$ to $\Delta V0$. Electric charge Q corresponding to the variation in the potential difference $\Delta V$ ($\Delta V0 - \Delta V1$) is released (read) from each radiation detecting element 7. In the following Expression (8), "C" indicates the electrostatic capacitance of each radiation detecting element 7.

$$Q = C \times (\Delta V0 - \Delta V1) \quad (8)$$

In this embodiment, the potential difference $\Delta V0$ between the signal line voltage Vs and the reverse bias voltage Vb at the time of the resetting process is changed to $\Delta V1$ during the electric charge accumulation mode before the reading process, as described above. This can simulate the condition where the electric charge Q is generated and accumulated in each radiation detecting element 7, without application of radiation to the radiographic image capturing apparatus 1 during a capturing operation.

When the radiation is applied to the radiographic image capturing apparatus 1 and the charge Q is accumulated in the radiation detecting elements 7, generation of a uniform electric charge Q in each radiation detecting element 7 or repeated generation of the same electric charge Q is difficult to be achieved through the application of radiation to the radiographic image capturing apparatus 1 because radiation applied to the radiation detecting elements 7 are different in intensity and the radiation detecting elements 7 have low capability to reproduce the electric charge Q (accumulated electric charge Q is likely to vary, despite a uniform application of X-ray radiation). In contrast, this embodiment enables the radiographic image capturing apparatus 1 to have a high capability to reproduce the electric charge Q.

At the end of the electric charge accumulation mode for a predetermined period, the controller 22 reads the electric charge Q accumulated in each radiation detecting element 7 in the form of a signal value S from each radiation detecting element 7, as in the reading process of the image data item D (refer to FIG. 6).

In this embodiment, the data read through such a manner is referred to as "signal value S", while the data read through the application of radiation to the radiographic image capturing apparatus 1 during a capturing operation (refer to FIG.

6) is referred to as "image data item D" to avoid confusion therebetween; however, the electric charge Q read from each radiation detecting element 7 in the form of a signal value S is identical to the electric charge Q read from each radiation detecting element 7 in the form of image data item D. If the capturing sequence is switched to another with a short on-time ΔTon and a low readout efficiency falling short of approximately 100%, the signal value S is read in the capturing sequence after the switching.

Since the readout efficiency varies depending on temperatures, the signal value S for the calculation of the readout efficiency should preferably be determined immediately before or after an actual capturing operation. Alternatively, if a variation in temperature of the panel is confirmed within a predetermined range with a monitor, the readout efficiency Ero may be calculated from the acquired signal value S to omit the time to determine the signal value S.

The signal values S should also undergo offset correction b. In a preferred embodiment, an image data item b for the offset correction is acquired before or after the determination of the signal value S to reduce errors in the offset correction b caused by dark electric charge, which varies depending on temperature.

[Calculation of Readout Efficiency Ero of Radiation Detecting Element 7]

Upon receipt of the signal value S read from the radiographic image capturing apparatus 1 through the procedure described above, the image processor 58 calculates the readout efficiency Ero of each radiation detecting element 7 of the radiographic image capturing apparatus 1 based on the received signal value S. The image processor 58 modifies the reference gain data ast for each radiation detecting element 7 (refer to the above Expression (5)) based on the calculated readout efficiency Ero of the radiation detecting element 7, corrects the image data item D with the modified reference gain data ast* (refer to the above Expressions (1) or (6)), and generates a radiographic image based on the corrected image data item D*, as described above.

[Method 1]

Methods of calculating the readout efficiency Ero of each radiation detecting element 7 of the radiographic image capturing apparatus 1 will now be described. In Method 1, a signal value S is read from each radiation detecting element 7 as described above during a capturing sequence with a long on-time ΔTon sufficient for a readout efficiency of approximately 100%, before the factory shipment of the radiographic image capturing apparatus 1. The read signal value S undergoes the offset correction and is stored (the resulting signal value S is referred to as a "signal value Sst"). The readout efficiency Ero of each radiation detecting element 7 can be calculated based on the received signal value S in accordance with the following Expression (9).

$$Ero = S/Sst \quad (9)$$

In Method 1, the signal value Sst at the time of factory shipment and the signal value S have a large value relative to noise. This can calculate the readout efficiency Ero at high precision.

[Method 2]

In Method 2, the radiographic image capturing apparatus 1 performs a procedure involving setting the potential difference to ΔV1, resetting the radiation detecting elements 7, accumulating electric charge, setting the potential difference to ΔV0, reading signal value S1, accumulating electric charge, and reading signal value S2 as illustrated in FIG. 13. The radiographic image capturing apparatus 1 sends the signal values S1 and S2 to the image processor 58.

In this case, a signal value S acquired by reading the electric charge Q at 100% from each radiation detecting element 7 is referred to as a "signal value S100". In the first reading process, the signal value S1 represented by S100×Ero is read, while the signal value represented by S100×(1−Ero) is not read. In the second reading process, the signal value is read which is calculated by multiplying the unread signal value S100×(1−Ero) in the first reading process by the readout efficiency Ero. In other words, the signal value S2 represented by S100×(1−Ero)×Ero is read in the second reading process.

Accordingly, the ratio of the signal value S1 to the signal value S2 can be represented by the following expression:

$$S1:S2 = S100 \times Ero : S100 \times (1-Ero) \times Ero$$

$$= 1:(1-Ero) \quad (10)$$

The readout efficiency Ero of each radiation detecting element 7 can be calculated in accordance with the following Expression (11), which is a transformation of the above Expression (10).

$$1 - Ero = S2/S1$$

$$\therefore Ero = 1 - S2/S1 \quad (11)$$

Method 2 can calculate the readout efficiency Ero of each radiation detecting element 7 without reading the signal value Sst before the factory shipment of the radiographic image capturing apparatus 1, unlike Method 1.

Furthermore, Method 2 can calculate the readout efficiency Ero with high precision despite variation in potential difference ΔV depending on temperatures.

[Method 3]

In Method 3, the procedure shown in FIG. 13 involving resetting the radiation detecting elements 7, accumulating electric charge, and reading signal value S is performed as in Method 2, and the radiographic image capturing apparatus 1 then reads the signal values S not once but multiple times, while the potential difference ΔV between the two electrodes 7a and 7b of each radiation detecting element 7 is kept at ΔV0.

In other words, signal values S can be read several times through the procedure involving setting the potential difference ΔV between the signal line voltage Vs and the reverse bias voltage Vb to ΔV0, resetting radiation detecting elements 7, accumulating electric charge, setting the potential difference ΔV to ΔV1, reading signal values S1, accumulating electric charge, reading signal values S2, accumulating electric charge, and reading signal values S3 (which continues to signal values Sn).

The image processor 58 approximates the signal values S1 to Sn in accordance with the following exponent function, for example, to calculate p and q (or only q):

$$Sn = p \cdot q^n \quad (n=1,2,\ldots) \quad (12)$$

As is evident from the above Expression (10), the following relation holds true:

$$Sn:Sn+1 = 1:(1-Ero)$$

Substitution of the above Expression (12) into this expression and subsequent transformation, as shown below, determines the readout efficiency Ero of each radiation detecting element 7:

$$Sn:Sn+1 = 1:(1-Ero) \quad (13)$$
$$= p \cdot qn : p \cdot qn + 1$$
$$= 1:q$$
$$1-Ero = q$$
$$\therefore Ero = 1-q$$

Method 3 reduces the impact of noise in each signal value S1 to Sn and thus can calculate the readout efficiency Ero of each radiation detecting element 7 at high precision.

[Method 4]

In the above case, the readout efficiency Ero of each radiation detecting element 7 is calculated as follows:

$$Ero = (S1-b)/\Sigma(Sn-b)$$
$$n = 1 - m \quad (14)$$

where m is a value that produces a readout efficiency of approximately 100% calculated by $\Sigma(Sn-b)$ (a value that meets: $\Delta Ton \times m \geq 6 \times$ time constant $\tau$, for example).

In the above description, the reference gain data ast and signal values Sst are determined before the factory shipment under the condition of an on-time $\Delta Ton$ sufficiently longer than the time constant $\tau$ and thus a readout efficiency of approximately 100%. Alternatively, the reference gain data ast and the read out efficiencies Ero_st may be determined under the condition of a short on-time $\Delta Ton$ and may be corrected in accordance with ast*=ast×Ero_st/Ero (refer to the above Expression (5)).

Before the factory shipment, these values may be determined multiple times and may be averaged to reduce the impact of noise and provide the values with high precision.

[Advantageous Effects]

The radiographic image capturing system 100 and the radiographic image capturing apparatus 1 according to this embodiment having the above configuration can automatically and accurately calculate the readout efficiencies Ero of the radiation detecting elements 7 of the radiographic image capturing apparatus 1, without the need for the operation by a radiological technician. The radiographic image capturing system 100 and the radiographic image capturing apparatus 1 can automatically and properly modify the reference gain data ast in accordance with the above Expression (5) based on the readout efficiency Ero of each radiation detecting element 7 to determine modified reference gain data ast*.

As described above, correction with the reference gain data ast after switching of the capturing sequences of the radiographic image capturing apparatus 1 or a variation in temperature in the radiographic image capturing apparatus 1 from a predetermined temperature to a temperature above a threshold value may provide corrected image data item D* having uneven image density (refer to FIG. 17B). In contrast, the radiographic image capturing apparatus 1 according to this embodiment modifies the reference gain data ast and corrects the image data item D with the modified reference gain data ast*. Correction with such a modified reference gain data ast* can provide corrected image data item D* without uneven image density (refer to FIG. 17A).

The radiographic image capturing system 100 and the radiographic image capturing apparatus 1 according to this embodiment automatically modify the reference gain data ast without the need for the operation by a radiological technician, as described above, and thus are very user-friendly to the radiological technician.

Such a modification of the reference gain data ast may be performed each time before or after a capturing operation involving a sequence with an on-time $\Delta Ton$ shorter than a predetermine value.

[Timing for Reading of Signal Values and Calculating Readout Efficiency of Radiation Detecting Element]

The reading process of signal values S in the radiographic image capturing apparatus 1 or the calculation of the readout efficiency Ero of each radiation detecting element 7 in the image processor 58 or the radiographic image capturing apparatus 1 may be performed when the radiographic image capturing apparatus 1 starts to perform a different capturing sequence (that is, when the capturing sequence is switched to another) or when a temperature in the radiographic image capturing apparatus 1 measured by the temperature sensor 25 varies from a predetermined temperature (i.e., a temperature in the radiographic image capturing apparatus 1, for example, before the factory shipment) to a temperature equal to or more than the threshold value (refer to FIG. 2 and FIG. 4).

Alternatively, the calculation of the readout efficiency Ero of each radiation detecting element 7 may be performed during installation of a new radiographic image capturing apparatus 1 in the radiographic image capturing system 100. In detail, the radiographic image capturing apparatus 1 sequentially switches capturing sequences operable in the radiographic image capturing system 100 to read signal values S and calculate the readout efficiency Ero (m) (m is a number assigned to the capturing sequence) of each radiation detecting element 7.

Figures 15, 16:
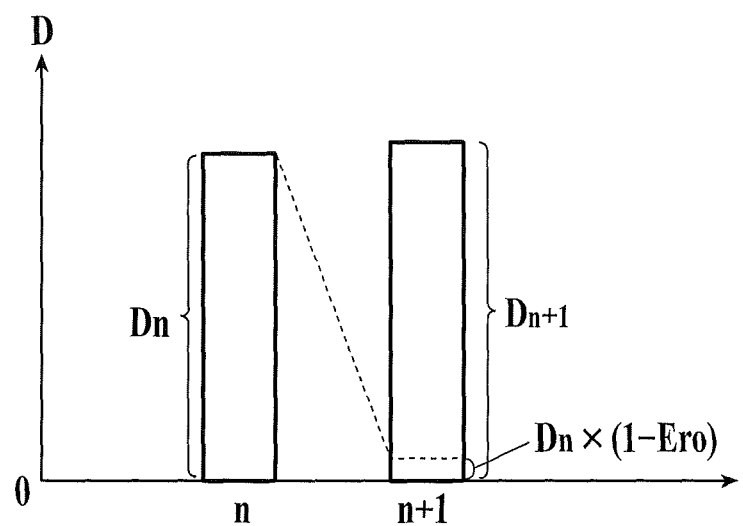
FIG. 15 is a table of a readout efficiency of each radiation detecting element determined and stored in a storage after each switching of capturing sequences.
FIG. 16 illustrates the presence of residual image data items unread in the nth capturing operation in the image data for the (n+1)th capturing operation.

The calculated readout efficiencies Ero(m) may be preliminarily stored in the storage unit 58c of the image processor 58 in the form of a table, as shown in FIG. 15. At the time of switching to another capturing sequence, the image processor 58 reads the readout efficiency Ero(m) of each radiation detecting element 7 corresponding to the switched capturing sequence from the storage unit 58c and then modifies the reference gain data ast for each radiation detecting element 7 for the correction of the gain of each radiation detecting element 7 (refer to FIG. 11 and the above Expression (5)).

If the readout efficiency Ero of each radiation detecting element 7 is calculated after variations in temperature in the radiographic image capturing apparatus 1 from a predetermined temperature to a temperature equal to or more than the threshold value, the calculated readout efficiency Ero(m) of each radiation detecting element 7 for each temperature difference between the temperature in the radiographic image capturing apparatus 1 and the predetermined temperature are tabulated (not shown), similar to the table as shown in FIG. 15. The image processor 58 may modify the reference gain data ast for correcting the gain of each radiation detecting element 7 with reference to the table.

[Removal of Residual Image Data from Multiple Radiographic Images Captured During Videographic Capturing]

In case of videographic capturing involving capturing of multiple radiographic images, residual image data of the radiographic image captured immediately before (or the radiographic image captured by one of the past capturing) may be left in each radiographic image. To address the problem of residual image data, the radiographic image capturing apparatus 1 according to this embodiment having the above configuration can calculate the readout efficiency Ero of each radiation detecting element 7 of the radiographic image capturing apparatus 1 at high precision, as described above.

The image processor 58 can remove residual image data from each radiographic image captured during videographic capturing with the readout efficiency Ero of each radiation detecting element 7. In the following description, the removal of residual image data is described in detail.

Each radiation detecting element 7 with a readout efficiency of Ero has an unreading rate of 1−Ero. Let each radiation detecting element 7 have an image data value of Dn in a radiographic image pn captured during the nth videographic capturing operation. Let each radiation detecting element 7 have an image data value of Dn+1 in a radiographic image pn+1 captured during the (n+1)th videographic capturing operation. As shown in FIG. 16, the unread image data (Dn×(1−Ero)) of the image data item Dn for the nth capturing operation is left as residual image data in the image data item Dn+1 for the (n+1)th capturing operation.

The image processor 58 can remove the residual image data of the image data item Dn from the image data item Dn+1 captured during the (n+1)th capturing operation for each radiation detecting element 7 of the radiographic image capturing apparatus 1 in accordance with the following Expression (15).

$$Dn+1^{**}=\{(Dn+1-O)-(Dn-O)\times(1-Ero)\}\times ast/Ero \qquad (15)$$

This configuration can properly remove the residual image data from multiple radiographic images captured during videographic capturing with the readout efficiency Ero of each radiation detecting element 7 determined at high precision in this embodiment.

In the above description, radiographic images are corrected with the modified gain data a. Alternatively, radiographic images may be corrected with the gain data a and second gain data (readout efficiency Ero) without any modification of these items. It should be understood that the embodiment described above is not construed to limit the present invention and can be appropriately modified without departing from the scope of the present invention.

The invention claimed is:

1. A radiographic image capturing system comprising:
   a radiographic image capturing apparatus comprising:
      a two-dimensional array of radiation detecting elements which each have a first electrode and a second electrode; and
      a control circuit which controls reading of image data from each of the radiation detecting elements based on a predetermined capturing sequence; and
   an image processor which has first gain data to correct gains of the radiation detecting elements in the radiographic image capturing apparatus, which corrects the image data based on the first gain data, and which generates a radiographic image based on the corrected image data, wherein
   a reverse bias voltage is applied to the first electrode of each of the radiation detecting elements of the radiographic image capturing apparatus,
   a corresponding signal line is connected to the second electrode of each of the radiation detecting elements via a switching element,
   the control circuit of the radiographic image capturing apparatus is capable of varying at least one of the reverse bias voltage and a signal line voltage to be applied to the corresponding signal line, and
   after resetting of the radiation detecting elements, the control circuit reads a signal value from each of the radiation detecting elements by varying at least one of the reverse bias voltage and the signal line voltage, creates second gain data based on the read signal value, and corrects the radiographic image with the first gain data and the second gain data.

2. The radiographic image capturing system according to claim 1, wherein after switching of the capturing sequence of the radiographic image capturing apparatus to another capturing sequence, the control circuit of the radiographic image capturing apparatus corrects a radiographic image with second gain data corresponding to the switched capturing sequence.

3. The radiographic image capturing system according to claim 1, wherein
   the radiographic image capturing apparatus comprises a temperature measuring device which measures a temperature in the radiographic image capturing apparatus, and
   if the temperature measuring device detects a variation of the temperature in the radiographic image capturing apparatus from a predetermined temperature to a temperature equal to or more than a threshold value, the control circuit of the radiographic image capturing apparatus corrects the radiographic image with second gain data corresponding to the temperature.

4. The radiographic image capturing system according to claim 1, wherein the image processor corrects unread data of the previous frame with the second gain data during a capturing sequence of videographic capturing with the radiographic image capturing apparatus.

5. A radiographic image capturing apparatus comprising:
   a two-dimensional array of radiation detecting elements which each have a first electrode and a second electrode; and
   a control circuit which controls reading of image data from each of the radiation detecting elements based on a predetermined capturing sequence, wherein
   a reverse bias voltage is applied to the first electrode of each of the radiation detecting elements,
   a corresponding signal line is connected to the second electrode of each of the radiation detecting elements via a switching element,
   the control circuit has first gain data to correct gains of the radiation detecting elements, corrects the image data based on the first gain data, and generates a radiographic image based on the corrected image data,
   the control circuit is capable of varying at least one of the reverse bias voltage and a signal line voltage to be applied to the corresponding signal line, and
   after the resetting of the radiation detecting elements, the control circuit reads a signal value from each of the radiation detecting elements by varying at least one of the reverse bias voltage and the signal line voltage, creates second gain data based on the read signal value, and corrects the radiographic image with the first gain data and the second gain data.

* * * * *